(12) United States Patent
Marion

(10) Patent No.: US 7,862,560 B2
(45) Date of Patent: Jan. 4, 2011

(54) ABLATION APPARATUS HAVING REDUCED NERVE STIMULATION AND RELATED METHODS

(75) Inventor: Duane W. Marion, Santa Clara, CA (US)

(73) Assignee: ArthroCare Corporation, Austin, TX (US)

( * ) Notice: Subject to any disclaimer, the term of this patent is extended or adjusted under 35 U.S.C. 154(b) by 954 days.

(21) Appl. No.: 11/690,449

(22) Filed: Mar. 23, 2007

(65) Prior Publication Data

US 2008/0234671 A1 Sep. 25, 2008

(51) Int. Cl.
*A61B 18/10* (2006.01)
*A61B 18/12* (2006.01)
*A61B 18/14* (2006.01)

(52) U.S. Cl. ............................... 606/34; 606/37; 606/41
(58) Field of Classification Search .................. 606/32, 606/37, 39, 40, 51–52
See application file for complete search history.

(56) References Cited

U.S. PATENT DOCUMENTS

| 2,050,904 | A | 4/1936 | Trice | 219/31 |
|---|---|---|---|---|
| 2,056,377 | A | 10/1939 | Wappler | 125/303 |
| 3,633,425 | A | 1/1972 | Sanford | 73/356 |
| 3,707,149 | A | 12/1972 | Hao et al. | 128/303.14 |
| 3,718,617 | A | 2/1973 | Royal | 260/30.4 |
| 3,815,604 | A | 6/1974 | O'Malley et al. | 128/305 |
| 3,828,780 | A | 8/1974 | Morrison, Jr. et al. | 128/275 |
| 3,901,242 | A | 8/1975 | Storz | 128/303 |
| 3,920,021 | A | 11/1975 | Hiltebrandt | 128/303 |
| 3,939,839 | A | 2/1976 | Curtiss | 128/303 |
| 3,963,030 | A | 6/1976 | Newton | 606/40 |
| 3,964,487 | A | 6/1976 | Judson | 606/39 |
| 3,970,088 | A | 7/1976 | Morrison | 128/303 |
| 4,033,351 | A | 7/1977 | Hetzel | 606/48 |
| 4,040,426 | A | 8/1977 | Morrison, Jr. | 128/303 |
| 4,043,342 | A | 8/1977 | Morrison, Jr. | 128/303 |
| 4,074,718 | A | 2/1978 | Morrison, Jr. | 128/303 |
| 4,092,986 | A | 6/1978 | Schneiderman | 128/303 |
| 4,114,623 | A | 9/1978 | Meinke et al. | 606/39 |
| 4,116,198 | A | 9/1978 | Roos | 128/303 |
| 4,181,131 | A | 1/1980 | Ogiu | 128/303 |
| 4,184,492 | A | 1/1980 | Meinke et al. | 128/303 |

(Continued)

FOREIGN PATENT DOCUMENTS

DE 3119735 1/1983

(Continued)

OTHER PUBLICATIONS

PCT Notification of the International Search Report and Written Opinion for PCT/US07/69856, 7pgs, Mailed Jun. 5, 2008.

(Continued)

*Primary Examiner*—Lee S Cohen
*Assistant Examiner*—Jaymi Della
(74) *Attorney, Agent, or Firm*—Matthew Scheele; Brian Szymczak

(57) ABSTRACT

Apparatus and methods for reducing nerve stimulation in electrosurgical instruments utilizing electrically isolated pairs of electrodes are disclosed. At least two pairs of electrodes may be configured to create at least two opposing currents which effectively cancel one another such that a net current flow is inhibited from developing within surrounding tissue structures to mitigate or eliminate undesired electrical stimulation of the tissue.

17 Claims, 5 Drawing Sheets

U.S. PATENT DOCUMENTS

| | | | | |
|---|---|---|---|---|
| 4,202,337 A | 5/1980 | Hren et al. | ............ | 128/303 |
| 4,228,800 A | 10/1980 | Degler, Jr. et al. | ............ | 128/303 |
| 4,232,676 A | 11/1980 | Herczog | ............ | 128/303 |
| 4,240,441 A | 12/1980 | Khalil | ............ | 600/505 |
| 4,248,231 A | 2/1981 | Herczog et al. | ............ | 128/303 |
| 4,301,801 A | 11/1981 | Schneiderman | ............ | 606/38 |
| 4,326,529 A | 4/1982 | Doss et al. | ............ | 128/303 |
| 4,346,715 A | 8/1982 | Gammell | ............ | 607/99 |
| 4,363,324 A | 12/1982 | Kusserow | ............ | 365/156 |
| 4,378,801 A * | 4/1983 | Oosten | ............ | 606/37 |
| 4,381,007 A | 4/1983 | Doss | ............ | 128/303 |
| 4,418,692 A | 12/1983 | Guay | ............ | 606/42 |
| 4,474,179 A | 10/1984 | Koch | ............ | 606/40 |
| 4,476,862 A | 10/1984 | Pao | ............ | 128/303 |
| 4,509,532 A | 4/1985 | DeVries | ............ | 128/736 |
| 4,520,818 A | 6/1985 | Mickiewicz | ............ | 606/40 |
| 4,532,924 A | 8/1985 | Auth et al. | ............ | 128/303 |
| 4,548,207 A | 10/1985 | Reimels | ............ | 128/303 |
| 4,567,890 A | 2/1986 | Ohta et al. | ............ | 128/303 |
| 4,572,206 A | 2/1986 | Geddes et al. | ............ | 600/505 |
| 4,580,557 A | 4/1986 | Hertzmann | ............ | 606/12 |
| 4,587,975 A | 5/1986 | Salo et al. | ............ | 600/506 |
| 4,590,934 A | 5/1986 | Malis et al. | ............ | 128/303 |
| 4,593,691 A | 6/1986 | Lindstrom et al. | ............ | 128/303 |
| 4,658,817 A | 4/1987 | Hardy | ............ | 606/14 |
| 4,660,571 A | 4/1987 | Hess et al. | ............ | 128/784 |
| 4,674,499 A | 6/1987 | Pao | ............ | 128/303 |
| 4,682,596 A | 7/1987 | Bales et al. | ............ | 128/303 |
| 4,706,667 A | 11/1987 | Roos | ............ | 128/303 |
| 4,709,698 A | 12/1987 | Johnston et al. | ............ | 606/41 |
| 4,727,874 A | 3/1988 | Bowers et al. | ............ | 128/303 |
| 4,750,902 A | 6/1988 | Wuchinich et al. | ............ | 604/22 |
| 4,765,331 A | 8/1988 | Petruzzi et al. | ............ | 128/303 |
| 4,785,823 A | 11/1988 | Eggers et al. | ............ | 128/692 |
| 4,805,616 A | 2/1989 | Pao | ............ | 128/303 |
| 4,823,791 A | 4/1989 | D'Amelio et al. | ............ | 123/303 |
| 4,832,048 A | 5/1989 | Cohen | ............ | 128/786 |
| 4,860,752 A | 8/1989 | Turner | ............ | 607/102 |
| 4,898,169 A | 2/1990 | Norman et al. | ............ | 606/42 |
| 4,907,589 A | 3/1990 | Cosman | ............ | 606/34 |
| 4,920,978 A | 5/1990 | Colvin | ............ | 128/784 |
| 4,931,047 A | 6/1990 | Broadwin et al. | ............ | 604/22 |
| 4,936,281 A | 6/1990 | Stasz | ............ | 128/660 |
| 4,936,301 A | 6/1990 | Rexroth et al. | ............ | 606/45 |
| 4,943,290 A | 7/1990 | Rexroth et al. | ............ | 606/45 |
| 4,955,377 A | 9/1990 | Lennox et al. | ............ | 607/105 |
| 4,966,597 A | 10/1990 | Cosman | ............ | 606/50 |
| 4,967,765 A | 11/1990 | Turner et al. | ............ | 128/785 |
| 4,976,711 A | 12/1990 | Parins et al. | ............ | 606/48 |
| 4,979,948 A | 12/1990 | Geddes et al. | ............ | 606/33 |
| 4,998,933 A | 3/1991 | Eggers et al. | ............ | 606/41 |
| 5,007,908 A | 4/1991 | Rydell | ............ | 606/47 |
| 5,009,656 A | 4/1991 | Reimels | ............ | 606/48 |
| 5,026,387 A | 6/1991 | Thomas | ............ | 606/169 |
| 5,035,696 A | 7/1991 | Rydell | ............ | 606/47 |
| 5,047,026 A | 9/1991 | Rydell | ............ | 606/48 |
| 5,047,027 A | 9/1991 | Rydell | ............ | 606/48 |
| 5,057,105 A | 10/1991 | Malone et al. | ............ | 606/28 |
| 5,057,106 A | 10/1991 | Kasevich et al. | ............ | 606/33 |
| 5,078,717 A | 1/1992 | Parins et al. | ............ | 606/48 |
| 5,080,660 A | 1/1992 | Buelna | ............ | 606/46 |
| 5,083,565 A | 1/1992 | Parins | ............ | 600/374 |
| 5,084,044 A | 1/1992 | Quint | ............ | 606/27 |
| 5,085,659 A | 2/1992 | Rydell | ............ | 606/47 |
| 5,088,997 A | 2/1992 | Delahuerga et al. | ............ | 606/42 |
| 5,092,339 A | 3/1992 | Geddes et al. | ............ | 606/505 |
| 5,098,431 A | 3/1992 | Rydell | ............ | 606/48 |
| 5,099,840 A | 3/1992 | Goble | ............ | 128/422 |
| 5,102,410 A | 4/1992 | Dressel | ............ | 606/15 |
| 5,108,391 A | 4/1992 | Flachenecker et al. | ............ | 606/38 |
| RE33,925 E | 5/1992 | Bales et al. | ............ | 606/48 |
| 5,112,330 A | 5/1992 | Nishigaki et al. | ............ | 606/46 |
| 5,122,138 A | 6/1992 | Manwaring | ............ | 606/46 |
| 5,125,928 A | 6/1992 | Parins et al. | ............ | 606/48 |
| 5,156,151 A | 10/1992 | Imran | ............ | 600/375 |
| 5,167,659 A | 12/1992 | Ohtomo et al. | ............ | 606/40 |
| 5,171,311 A | 12/1992 | Rydell et al. | ............ | 606/48 |
| 5,174,304 A | 12/1992 | Latina et al. | ............ | 607/141 |
| 5,178,620 A | 1/1993 | Eggers et al. | ............ | 606/41 |
| 5,183,338 A | 2/1993 | Wickersheim et al. | ............ | 374/131 |
| 5,190,517 A | 3/1993 | Zieve et al. | ............ | 604/22 |
| 5,192,280 A | 3/1993 | Parins | ............ | 606/48 |
| 5,195,959 A | 3/1993 | Smith | ............ | 604/34 |
| 5,197,466 A | 3/1993 | Marchosky et al. | ............ | 128/399 |
| 5,197,963 A | 3/1993 | Parins | ............ | 606/46 |
| 5,207,675 A | 5/1993 | Canady | ............ | 606/40 |
| 5,217,457 A | 6/1993 | Delahuerga et al. | ............ | 606/42 |
| 5,217,459 A | 6/1993 | Kamerling | ............ | 606/48 |
| 5,249,585 A | 10/1993 | Turner et al. | ............ | 607/99 |
| 5,255,980 A | 10/1993 | Thomas et al. | ............ | 374/161 |
| 5,261,410 A | 11/1993 | Alfano et al. | ............ | 600/475 |
| 5,267,994 A | 12/1993 | Gentelia et al. | ............ | 606/15 |
| 5,267,997 A | 12/1993 | Farin et al. | ............ | 606/38 |
| 5,273,524 A | 12/1993 | Fox et al. | ............ | 604/21 |
| 5,277,201 A | 1/1994 | Stern | ............ | 607/98 |
| 5,281,216 A | 1/1994 | Klicek | ............ | 606/42 |
| 5,281,218 A | 1/1994 | Imran | ............ | 606/41 |
| 5,282,799 A | 2/1994 | Rydell | ............ | 606/48 |
| 5,290,282 A | 3/1994 | Casscells | ............ | 606/29 |
| 5,300,069 A | 4/1994 | Hunsberger et al. | ............ | 606/37 |
| 5,306,238 A | 4/1994 | Fleenor | ............ | 606/42 |
| 5,312,400 A | 5/1994 | Bales et al. | ............ | 606/41 |
| 5,314,406 A | 5/1994 | Arias et al. | ............ | 604/21 |
| 5,318,563 A | 6/1994 | Malis et al. | ............ | 606/38 |
| 5,324,254 A | 6/1994 | Phillips | ............ | 604/21 |
| 5,330,470 A | 7/1994 | Hagen | ............ | 606/42 |
| 5,334,140 A | 8/1994 | Philips | ............ | 604/35 |
| 5,334,183 A | 8/1994 | Wuchinich | ............ | 606/46 |
| 5,334,193 A | 8/1994 | Nardella | ............ | 606/41 |
| 5,336,220 A | 8/1994 | Ryan et al. | ............ | 604/22 |
| 5,336,443 A | 8/1994 | Odashima | ............ | 252/511 |
| 5,342,357 A | 8/1994 | Nardella | ............ | 606/40 |
| 5,348,554 A | 9/1994 | Imran et al. | ............ | 606/41 |
| 5,366,443 A | 11/1994 | Eggers et al. | ............ | 604/114 |
| 5,370,675 A | 12/1994 | Edwards et al. | ............ | 607/101 |
| 5,374,261 A | 12/1994 | Yoon | ............ | 604/385.01 |
| 5,375,588 A | 12/1994 | Yoon | ............ | 128/4 |
| 5,380,277 A | 1/1995 | Phillips | ............ | 604/33 |
| 5,380,316 A | 1/1995 | Aita | ............ | 606/7 |
| 5,383,876 A | 1/1995 | Nardella | ............ | 606/49 |
| 5,383,917 A | 1/1995 | Desai et al. | ............ | 607/702 |
| 5,389,096 A | 2/1995 | Aita | ............ | 606/15 |
| 5,395,312 A | 3/1995 | Desai | ............ | 604/22 |
| 5,400,267 A | 3/1995 | Denen et al. | ............ | 702/59 |
| 5,401,272 A | 3/1995 | Perkins | ............ | 606/15 |
| 5,403,311 A | 4/1995 | Abele et al. | ............ | 606/49 |
| 5,417,687 A | 5/1995 | Nardella et al. | ............ | 606/32 |
| 5,419,767 A | 5/1995 | Eggers et al. | ............ | 604/114 |
| 5,423,810 A | 6/1995 | Goble et al. | ............ | 606/40 |
| 5,423,882 A | 6/1995 | Jackman et al. | ............ | 607/122 |
| 5,436,566 A | 7/1995 | Thompson et al. | ............ | 324/713 |
| 5,437,662 A | 8/1995 | Nardella | ............ | 606/40 |
| 5,438,302 A | 8/1995 | Goble | ............ | 331/167 |
| 5,441,499 A | 8/1995 | Fritzsch | ............ | 606/45 |
| 5,449,356 A | 9/1995 | Walbrink et al. | ............ | 606/49 |
| 5,451,224 A | 9/1995 | Goble et al. | ............ | 606/48 |
| 5,454,809 A | 10/1995 | Janssen | ............ | 606/41 |
| 5,458,596 A | 10/1995 | Lax et al. | ............ | 606/31 |
| 5,458,597 A | 10/1995 | Edwards et al. | ............ | 606/41 |
| 5,472,443 A | 12/1995 | Cordis et al. | ............ | 606/48 |
| 5,486,161 A | 1/1996 | Lax et al. | ............ | 604/22 |
| 5,496,312 A | 3/1996 | Klicek | ............ | 606/34 |
| 5,496,314 A | 3/1996 | Eggers | ............ | 606/41 |
| 5,496,317 A | 3/1996 | Goble et al. | ............ | 606/48 |

| Patent No. | Date | Inventor | Class |
|---|---|---|---|
| 5,505,730 A | 4/1996 | Edwards et al. | 606/41 |
| 5,507,743 A | 4/1996 | Edwards et al. | 313/639 |
| 5,514,130 A | 5/1996 | Baker | 606/41 |
| 5,540,683 A | 7/1996 | Ichikawa et al. | 606/40 |
| 5,542,915 A | 8/1996 | Edwards et al. | 604/22 |
| 5,549,598 A | 8/1996 | O'Donnell, Jr. | 606/6 |
| 5,554,152 A | 9/1996 | Aita | 606/7 |
| 5,556,397 A | 9/1996 | Long et al. | 606/48 |
| 5,562,703 A | 10/1996 | Desai | 606/210 |
| 5,569,242 A | 10/1996 | Lax et al. | 606/42 |
| 5,571,100 A | 11/1996 | Goble et al. | 606/41 |
| 5,573,533 A | 11/1996 | Strul | 606/34 |
| 5,584,872 A | 12/1996 | LaFontaine et al. | 607/117 |
| 5,588,960 A | 12/1996 | Edwards et al. | 604/20 |
| 5,599,350 A | 2/1997 | Schulze et al. | 606/51 |
| 5,609,151 A | 3/1997 | Mulier et al. | 128/642 |
| 5,633,578 A | 5/1997 | Eggers et al. | 323/301 |
| 5,634,921 A | 6/1997 | Hood et al. | 606/5 |
| 5,643,304 A | 7/1997 | Schechter et al. | 606/171 |
| 5,647,869 A | 7/1997 | Goble et al. | 606/37 |
| 5,658,278 A | 8/1997 | Imran et al. | 606/41 |
| 5,660,567 A | 8/1997 | Nierlich et al. | 439/620.21 |
| 5,662,680 A | 9/1997 | Desai | 606/210 |
| 5,676,693 A | 10/1997 | LaFontaine | 607/116 |
| 5,681,282 A | 10/1997 | Eggers et al. | 604/114 |
| 5,683,366 A | 11/1997 | Eggers et al. | 604/114 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,697,927 A | 12/1997 | Imran et al. | 606/41 |
| 5,700,262 A | 12/1997 | Acosta et al. | 606/48 |
| 5,715,817 A | 2/1998 | Stevens-Wright et al. | 600/373 |
| 5,722,975 A | 3/1998 | Edwards et al. | 606/41 |
| 5,725,524 A | 3/1998 | Mulier et al. | 606/41 |
| 5,749,869 A | 5/1998 | Lindenmeier et al. | 606/34 |
| 5,749,871 A | 5/1998 | Hood et al. | 606/50 |
| 5,749,914 A | 5/1998 | Janssen | 607/116 |
| 5,755,753 A | 5/1998 | Knowlton | 607/98 |
| 5,766,153 A | 6/1998 | Eggers et al. | 604/114 |
| 5,769,847 A | 6/1998 | Panescu et al. | 606/42 |
| 5,785,705 A | 7/1998 | Baker | 606/32 |
| 5,786,578 A | 7/1998 | Christy et al. | 219/720 |
| 5,800,429 A | 9/1998 | Edwards | 606/41 |
| 5,807,395 A | 9/1998 | Mulier et al. | 606/41 |
| 5,810,764 A | 9/1998 | Eggers et al. | 604/23 |
| 5,810,802 A | 9/1998 | Panescu et al. | 606/31 |
| 5,810,809 A | 9/1998 | Rydell | 606/49 |
| 5,836,875 A | 11/1998 | Webster, Jr. | 600/374 |
| 5,843,019 A | 12/1998 | Eggers et al. | 604/22 |
| 5,860,951 A | 1/1999 | Eggers | 604/510 |
| 5,860,974 A | 1/1999 | Abele | 606/41 |
| 5,860,975 A | 1/1999 | Goble et al. | 606/45 |
| 5,871,469 A | 2/1999 | Eggers et al. | 604/114 |
| 5,873,855 A | 2/1999 | Eggers et al. | 604/114 |
| 5,873,877 A | 2/1999 | McGaffigan | 606/41 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,891,134 A | 4/1999 | Goble et al. | 606/27 |
| 5,897,553 A | 4/1999 | Mulier | 606/41 |
| 5,902,272 A | 5/1999 | Eggers et al. | 604/114 |
| 5,944,715 A | 8/1999 | Goble et al. | 606/41 |
| 5,954,716 A | 9/1999 | Sharkey et al. | 606/32 |
| 5,964,786 A | 10/1999 | Ochs et al. | 607/5 |
| 6,004,319 A | 12/1999 | Goble et al. | 606/48 |
| 6,013,076 A | 1/2000 | Goble et al. | 606/41 |
| 6,015,406 A | 1/2000 | Goble et al. | 606/41 |
| 6,024,733 A | 2/2000 | Eggers et al. | 604/500 |
| 6,027,501 A | 2/2000 | Goble et al. | 606/41 |
| 6,039,734 A | 3/2000 | Goble et al. | 606/41 |
| 6,047,700 A | 4/2000 | Eggers et al. | 128/898 |
| 6,056,746 A | 5/2000 | Goble et al. | 606/48 |
| 6,063,079 A | 5/2000 | Hovda et al. | 606/41 |
| 6,066,134 A | 5/2000 | Eggers et al. | 606/32 |
| 6,068,628 A | 5/2000 | Fanton et al. | 606/41 |
| 6,074,386 A | 6/2000 | Goble et al. | 606/34 |
| 6,090,106 A | 7/2000 | Goble et al. | 606/41 |
| 6,093,186 A | 7/2000 | Goble et al. | 606/34 |
| 6,102,046 A | 8/2000 | Weinstein et al. | 128/898 |
| 6,105,581 A | 8/2000 | Eggers et al. | 128/898 |
| 6,109,268 A | 8/2000 | Thapliyal et al. | 128/898 |
| 6,117,109 A | 9/2000 | Eggers et al. | 604/114 |
| 6,126,682 A | 10/2000 | Sharkey et al. | 607/96 |
| 6,142,992 A | 11/2000 | Cheng et al. | 606/34 |
| 6,149,620 A | 11/2000 | Baker et al. | 604/22 |
| 6,159,194 A | 12/2000 | Eggers et al. | 604/500 |
| 6,159,208 A | 12/2000 | Hovda et al. | 606/41 |
| 6,162,217 A | 12/2000 | Kannenberg et al. | 606/34 |
| 6,168,593 B1 | 1/2001 | Sharkey et al. | 606/34 |
| 6,174,309 B1 | 1/2001 | Wrublewski et al. | 606/45 |
| 6,179,824 B1 | 1/2001 | Eggers et al. | 604/500 |
| 6,179,836 B1 | 1/2001 | Eggers et al. | 606/45 |
| 6,183,469 B1 | 2/2001 | Thapliyal et al. | 606/41 |
| 6,190,381 B1 | 2/2001 | Olsen et al. | 606/32 |
| 6,197,021 B1 | 3/2001 | Panescu et al. | 606/31 |
| 6,203,542 B1 | 3/2001 | Ellsberry et al. | 606/41 |
| 6,210,402 B1 | 4/2001 | Olsen et al. | 606/32 |
| 6,210,405 B1 | 4/2001 | Goble et al. | 606/41 |
| 6,224,592 B1 | 5/2001 | Eggers et al. | 606/32 |
| 6,228,078 B1 | 5/2001 | Eggers | 606/32 |
| 6,228,081 B1 | 5/2001 | Goble | 606/34 |
| 6,234,178 B1 | 5/2001 | Goble et al. | 606/32 |
| 6,235,020 B1 | 5/2001 | Cheng et al. | 606/34 |
| 6,237,604 B1 | 5/2001 | Burnside et al. | 128/897 |
| 6,238,391 B1 | 5/2001 | Olsen et al. | 606/41 |
| 6,238,393 B1 | 5/2001 | Mulier et al. | 606/41 |
| 6,254,600 B1 | 7/2001 | Willink et al. | 606/41 |
| 6,261,286 B1 | 7/2001 | Goble et al. | 606/34 |
| 6,261,311 B1 | 7/2001 | Sharkey et al. | 607/96 |
| 6,264,652 B1 | 7/2001 | Eggers et al. | 606/41 |
| 6,270,460 B1 | 8/2001 | McCartan et al. | 600/459 |
| 6,277,112 B1 | 8/2001 | Underwood et al. | 606/32 |
| 6,280,441 B1 | 8/2001 | Ryan | 606/45 |
| 6,283,961 B1 | 9/2001 | Underwood et al. | 604/41 |
| 6,293,942 B1 | 9/2001 | Goble et al. | 606/38 |
| 6,296,636 B1 | 10/2001 | Cheng et al. | 606/32 |
| 6,296,638 B1 | 10/2001 | Davison et al. | 606/41 |
| 6,306,134 B1 | 10/2001 | Goble et al. | 606/42 |
| 6,308,089 B1 | 10/2001 | von der Rur et al. | 600/338 |
| 6,309,387 B1 | 10/2001 | Eggers et al. | 606/41 |
| 6,312,408 B1 | 11/2001 | Eggers et al. | 604/114 |
| 6,322,549 B1 | 11/2001 | Eggers et al. | 604/500 |
| 6,346,104 B2 | 2/2002 | Daly et al. | 606/34 |
| 6,346,107 B1 | 2/2002 | Cucin | 606/49 |
| 6,355,032 B1 | 3/2002 | Hovda et al. | 606/32 |
| 6,363,937 B1 | 4/2002 | Hovda et al. | 128/898 |
| 6,364,877 B1 | 4/2002 | Goble et al. | 606/34 |
| 6,379,351 B1 | 4/2002 | Thapliyal et al. | 606/41 |
| 6,391,025 B1 | 5/2002 | Weinstein et al. | 606/41 |
| 6,409,722 B1 | 6/2002 | Hoey et al. | 606/34 |
| 6,416,507 B1 | 7/2002 | Eggers et al. | 606/32 |
| 6,416,508 B1 | 7/2002 | Eggers et al. | 606/32 |
| 6,416,509 B1 | 7/2002 | Goble et al. | 606/37 |
| 6,432,103 B1 | 8/2002 | Ellsberry et al. | 606/41 |
| 6,440,129 B1 | 8/2002 | Simpson | 606/42 |
| 6,468,274 B1 | 10/2002 | Alleyne et al. | 606/32 |
| 6,468,275 B1 | 10/2002 | Wampler et al. | 606/48 |
| 6,482,201 B1 | 11/2002 | Olsen et al. | 606/41 |
| 6,514,250 B1 | 2/2003 | Jahns et al. | 606/41 |
| 6,517,498 B1 | 2/2003 | Burbank et al. | 600/564 |
| 6,530,922 B2 | 3/2003 | Cosman | 606/34 |
| 6,558,382 B2 | 5/2003 | Jahns et al. | 606/41 |
| 6,565,560 B1 | 5/2003 | Goble et al. | 606/41 |
| 6,578,579 B2 | 6/2003 | Burnside | 128/897 |
| 6,589,237 B2 | 7/2003 | Woloszko et al. | 606/41 |

| Patent No. | Date | Inventor | Class |
|---|---|---|---|
| 6,602,248 B1 | 8/2003 | Sharps et al. | 606/32 |
| 6,620,156 B1 | 9/2003 | Garito et al. | 606/50 |
| 6,632,193 B1 | 10/2003 | Davison et al. | 604/22 |
| 6,632,220 B1 | 10/2003 | Eggers et al. | 606/41 |
| 6,635,034 B1 | 10/2003 | Cosmescu | 604/289 |
| 6,730,080 B2 | 5/2004 | Harano et al. | 606/38 |
| 6,749,604 B1 | 6/2004 | Eggers et al. | 606/41 |
| 6,749,608 B2 | 6/2004 | Garito et al. | 606/45 |
| 6,770,071 B2 | 8/2004 | Woloszko et al. | 606/41 |
| 6,780,178 B2 | 8/2004 | Palanker et al. | 600/41 |
| 6,780,180 B1 | 8/2004 | Goble et al. | 606/41 |
| 6,802,842 B2 | 10/2004 | Ellman et al. | 606/45 |
| 6,837,887 B2 | 1/2005 | Woloszko et al. | 606/41 |
| 6,837,888 B2 | 1/2005 | Ciarrocca et al. | 606/41 |
| 6,866,671 B2 | 3/2005 | Tierney et al. | 606/130 |
| 6,878,149 B2 | 4/2005 | Gatto | 606/46 |
| 6,890,307 B2 | 5/2005 | Kokate et al. | 600/549 |
| 6,892,086 B2 | 5/2005 | Russell | 600/372 |
| 6,911,027 B1 | 6/2005 | Edwards et al. | 606/40 |
| 6,920,883 B2 | 7/2005 | Bessette et al. | 128/898 |
| 6,929,640 B1 | 8/2005 | Underwood et al. | 606/32 |
| 6,949,096 B2 | 9/2005 | Davison et al. | 606/41 |
| 6,960,204 B2 | 11/2005 | Eggers et al. | 606/32 |
| 6,974,453 B2 | 12/2005 | Woloszko et al. | 606/41 |
| 6,979,328 B2 | 12/2005 | Baerveldt et al. | 606/6 |
| 6,979,601 B2 | 12/2005 | Marr et al. | 438/132 |
| 6,984,231 B2 | 1/2006 | Goble et al. | 606/37 |
| 6,986,770 B2 | 1/2006 | Hood | 451/6 |
| 6,991,631 B2 | 1/2006 | Woloszko et al. | 606/41 |
| 7,001,382 B2 * | 2/2006 | Gallo, Sr. | 606/41 |
| 7,004,941 B2 | 2/2006 | Tvinnereim et al. | 606/41 |
| 7,010,353 B2 | 3/2006 | Gan et al. | 607/50 |
| 7,041,102 B2 | 5/2006 | Truckai et al. | 606/51 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,094,231 B1 | 8/2006 | Ellman et al. | 606/37 |
| 7,104,986 B2 | 9/2006 | Hovda et al. | 606/32 |
| 7,115,139 B2 | 10/2006 | McClurken et al. | 607/96 |
| 7,131,969 B1 | 11/2006 | Hovda et al. | 606/45 |
| 7,169,143 B2 | 1/2007 | Eggers et al. | 606/32 |
| 7,179,255 B2 | 2/2007 | Lettice et al. | 606/32 |
| 7,186,234 B2 | 3/2007 | Dahla et al. | 604/22 |
| 7,192,428 B2 | 3/2007 | Eggers et al. | 606/41 |
| 7,201,750 B1 | 4/2007 | Eggers et al. | 606/41 |
| 7,217,268 B2 | 5/2007 | Eggers et al. | 606/32 |
| 7,247,155 B2 | 7/2007 | Hoey et al. | 606/34 |
| 7,270,658 B2 | 9/2007 | Woloszko et al. | 606/32 |
| 7,278,994 B2 | 10/2007 | Goble | 606/41 |
| 7,282,048 B2 | 10/2007 | Goble et al. | 606/34 |
| 7,335,199 B2 | 2/2008 | Goble et al. | 606/41 |
| 7,344,532 B2 | 3/2008 | Goble et al. | 606/34 |
| 7,678,069 B1 | 3/2010 | Baker et al. | 604/22 |
| 7,691,101 B2 | 4/2010 | Davison et al. | 606/41 |
| 2002/0029036 A1 | 3/2002 | Goble et al. | 606/38 |
| 2002/0042612 A1 | 4/2002 | Hood et al. | 606/50 |
| 2002/0095151 A1 | 7/2002 | Dahla et al. | 606/41 |
| 2002/0115997 A1 * | 8/2002 | Truckai et al. | 606/51 |
| 2002/0151882 A1 | 10/2002 | Marko et al. | 606/28 |
| 2002/0183739 A1 | 12/2002 | Long | 606/41 |
| 2003/0013986 A1 | 1/2003 | Saadat | 600/549 |
| 2003/0014045 A1 | 1/2003 | Russell | 606/41 |
| 2003/0014047 A1 | 1/2003 | Woloszko et al. | 606/41 |
| 2003/0028189 A1 | 2/2003 | Woloszko et al. | 604/45 |
| 2003/0088245 A1 | 5/2003 | Woloszko et al. | 606/41 |
| 2003/0130655 A1 | 7/2003 | Woloszko et al. | 606/45 |
| 2003/0158545 A1 | 8/2003 | Hovda et al. | 606/32 |
| 2003/0171743 A1 | 9/2003 | Tasto et al. | 606/32 |
| 2003/0181903 A1 | 9/2003 | Hood et al. | 606/49 |
| 2003/0208194 A1 | 11/2003 | Hovda et al. | 606/41 |
| 2003/0208196 A1 | 11/2003 | Stone | 606/41 |
| 2003/0212396 A1 | 11/2003 | Eggers et al. | 606/41 |
| 2003/0216725 A1 | 11/2003 | Woloszko et al. | 606/41 |
| 2003/0216732 A1 | 11/2003 | Truckai et al. | 606/49 |
| 2004/0024399 A1 | 2/2004 | Sharps et al. | 606/32 |
| 2004/0030330 A1 | 2/2004 | Brassell et al. | 606/41 |
| 2004/0049180 A1 | 3/2004 | Sharps et al. | 606/32 |
| 2004/0054366 A1 | 3/2004 | Davison et al. | 606/45 |
| 2004/0116922 A1 | 6/2004 | Hovda et al. | 606/41 |
| 2004/0127893 A1 | 7/2004 | Hovda | 606/41 |
| 2004/0153057 A1 | 8/2004 | Davison | 600/410 |
| 2004/0186469 A1 | 9/2004 | Woloszko et al. | 606/41 |
| 2004/0230190 A1 | 11/2004 | Dahla et al. | 604/41 |
| 2005/0004634 A1 | 1/2005 | Hovda et al. | 606/41 |
| 2005/0010205 A1 | 1/2005 | Hovda et al. | 606/32 |
| 2005/0033278 A1 | 2/2005 | McClurken et al. | 606/34 |
| 2005/0119650 A1 | 6/2005 | Sanders et al. | 424/426 |
| 2005/0131402 A1 | 6/2005 | Ciarrocca et al. | 600/450 |
| 2005/0187543 A1 | 8/2005 | Underwood et al. | 606/41 |
| 2005/0234439 A1 | 10/2005 | Underwood et al. | 606/32 |
| 2005/0251134 A1 | 11/2005 | Woloszko et al. | 606/32 |
| 2005/0261754 A1 | 11/2005 | Woloszko et al. | 606/32 |
| 2005/0273091 A1 * | 12/2005 | Booth et al. | 606/41 |
| 2005/0288665 A1 | 12/2005 | Woloszko et al. | 606/41 |
| 2006/0036237 A1 | 2/2006 | Davison et al. | 606/41 |
| 2006/0095026 A1 | 5/2006 | Hovda et al. | 606/32 |
| 2006/0095031 A1 | 5/2006 | Ormsby | 606/34 |
| 2006/0129145 A1 | 6/2006 | Ormsby et al. | 606/41 |
| 2006/0178670 A1 | 8/2006 | Woloszko et al. | 606/48 |
| 2006/0189971 A1 | 8/2006 | Eggers et al. | 606/32 |
| 2006/0253117 A1 | 11/2006 | Hovda et al. | 128/898 |
| 2006/0259025 A1 | 11/2006 | Dahla | 607/108 |
| 2007/0010808 A1 | 1/2007 | Dahla | 606/41 |
| 2007/0010809 A1 | 1/2007 | Hovda et al. | 606/32 |
| 2007/0106288 A1 | 5/2007 | Woloszko et al. | 606/41 |
| 2007/0112346 A1 | 5/2007 | Underwood et al. | 606/41 |
| 2007/0112348 A1 | 5/2007 | Eggers et al. | 606/41 |
| 2007/0129715 A1 | 6/2007 | Eggers et al. | 606/32 |
| 2007/0149966 A1 | 6/2007 | Dahla et al. | 606/41 |
| 2007/0161981 A1 | 7/2007 | Sanders et al. | 606/41 |
| 2007/0179497 A1 | 8/2007 | Eggers et al. | 606/41 |
| 2007/0208334 A1 | 9/2007 | Woloszko et al. | 606/41 |
| 2007/0208335 A1 | 9/2007 | Woloszko et al. | 606/41 |
| 2007/0213700 A1 | 9/2007 | Davison et al. | 606/32 |
| 2007/0282323 A1 | 12/2007 | Woloszko et al. | 606/41 |
| 2008/0004621 A1 | 1/2008 | Dahla et al. | 606/48 |
| 2008/0077128 A1 | 3/2008 | Woloszko et al. | 606/41 |
| 2008/0154255 A1 * | 6/2008 | Panos et al. | 606/33 |
| 2008/0167645 A1 | 7/2008 | Woloszko | 606/40 |
| 2008/0243116 A1 * | 10/2008 | Anderson | 606/41 |
| 2008/0300590 A1 * | 12/2008 | Horne et al. | 606/35 |
| 2009/0209956 A1 | 8/2009 | Marion | 606/34 |
| 2010/0152726 A1 | 6/2010 | Cadouri et al. | 606/41 |

FOREIGN PATENT DOCUMENTS

| | | |
|---|---|---|
| DE | 3930451 A1 | 3/1991 |
| EP | 423757 | 3/1996 |
| EP | 0703461 A2 | 3/1996 |
| EP | 0740926 A2 | 11/1996 |
| EP | 0 754 437 | 1/1997 |
| EP | 0 694 290 | 11/2000 |
| EP | 1334699 | 8/2003 |
| EP | 1428480 | 6/2004 |
| EP | 1707147 | 10/2006 |
| FR | 2313949 | 1/1977 |
| GB | 467502 | 6/1937 |
| GB | 2160102 A * | 12/1985 |
| GB | 2299216 | 9/1996 |
| GB | 2 308 979 | 7/1997 |
| GB | 2 308 980 | 7/1997 |
| GB | 2 308 981 | 7/1997 |
| GB | 2 327 350 | 1/1999 |
| GB | 2 327 351 | 1/1999 |
| GB | 2 327 352 | 1/1999 |
| GB | 2333455 | 7/1999 |

| | | |
|---|---|---|
| GB | 2406793 | 4/2005 |
| JP | 57-57802 | 4/1982 |
| JP | 57-117843 | 7/1982 |
| NL | 05/000434 | 12/2006 |
| WO | 90/03152 | 4/1990 |
| WO | 90/07303 | 7/1990 |
| WO | 92/21278 | 12/1992 |
| WO | 93/13816 | 7/1993 |
| WO | 93/20747 | 10/1993 |
| WO | 94/04220 | 3/1994 |
| WO | 94/08654 | 4/1994 |
| WO | 94/10921 | 5/1994 |
| WO | 94/26228 | 11/1994 |
| WO | 95/34259 | 12/1995 |
| WO | 96/00040 | 1/1996 |
| WO | 96/00042 | 1/1996 |
| WO | 96/39086 | 12/1996 |
| WO | 97/00646 | 1/1997 |
| WO | 97/00647 | 1/1997 |
| WO | 97/18768 | 5/1997 |
| WO | 97/24073 | 7/1997 |
| WO | 97/24074 | 7/1997 |
| WO | 97/24993 | 7/1997 |
| WO | 97/24994 | 7/1997 |
| WO | 97/43971 | 11/1997 |
| WO | 97/48345 | 12/1997 |
| WO | 97/48346 | 12/1997 |
| WO | 98/07468 | 2/1998 |
| WO | 98/26724 | 6/1998 |
| WO | 98/27879 | 7/1998 |
| WO | 98/27880 | 7/1998 |
| WO | 99/20213 | 4/1999 |
| WO | 99/51155 | 10/1999 |
| WO | 99/51158 | 10/1999 |
| WO | 99/56648 | 11/1999 |
| WO | 00/00098 | 1/2000 |
| WO | 00/09053 | 2/2000 |
| WO | 01/24720 | 4/2001 |
| WO | 01/87154 | 5/2001 |
| WO | 02/36028 | 5/2002 |
| WO | 02/102255 | 12/2002 |
| WO | 03/024305 | 3/2003 |
| WO | 03/092477 | 11/2003 |
| WO | 2004/026150 | 4/2004 |
| WO | 2004/071278 | 8/2004 |
| WO | 2005/125287 | 12/2005 |
| WO | 2007/006000 | 1/2007 |
| WO | 2007/056729 | 5/2007 |

OTHER PUBLICATIONS

UK Search Report for GB0805062.7, 1 pg, Jul. 16, 2008.
European Search Report for EP 02773432 3pgs, Dec. 19, 2008.
European Examination Report for EP 05024974 4 pgs, Dec. 5, 2008.
UK Search Report for GB0800129.9 2pgs, May 8, 2008.
European Search Report for EP 04708664.0 5pgs, Apr. 6, 2009.
BiLAP IFU 910033-002 Rev A for BiLAP Model 3527, L-Hook; BiLAP Model 3525, J-Hook; BiLAP Model 3529, High Angle, 2 pgs, Nov. 30, 1993.
BiLAP IFU 910026-001 Rev A for BiLAP Model 3525, J-Hook, 4 pgs, May 20, 1991.
BiLAP Generator Settings, Jun. 1991.
Tucker et al. "The interaction between electrosurgical generators, endroscopic electrodes, and tissue," Gastrointestinal Endoscopy, vol. 38, No. 2, pp. 118-122, 1992.
Buchelt, et al. "Excimer Laser Ablation of Fibrocartilage: An In Vitro and In Vivo Study", Lasers in Surgery and Medicine, vol. 11, pp. 271-279, 1991.
Costello et al., "Nd: YAG Laser Ablation of the Prostate as a Treatment for Benign Prostatic Hypertrophy", Lasers in Surgery and Medicine, vol. 12, pp. 121-124, 1992.
Rand et al., "Effect of Elecctrocautery on Fresh Human Articular Cartilage", J. Arthro. Surg., vol. 1, pp. 242-246, 1985.

O'Neill et al., "Percutaneous Plasma Discectomy Stimulates Repair in Injured Porcine Intervertebral Discs", Dept. of Orthopaedic Surgery, Dept. of Radiology Univ. of Cal at San Francisco, CA, 3 pgs.
PCT International Search Report for PCT/US99/14685, 1 pg, Mailed Oct. 21, 1999.
PCT Notification of International Preliminary Examination Report for PCT/US99/14685, 4 pgs, Mailed Feb. 20, 2001.
PCT International Search Report for PCT/US98/22323, 1 pg, Mailed Mar. 3, 1999.
PCT Notification of International Preliminary Examination Report for PCT/US98/22323, 5 pgs, Mailed Nov. 28, 2000.
European Search Report for EP 98953859, 2 pgs, Jul. 2, 2001.
Supplementary European Search Report for EP 98953859, 3 pgs, Oct. 18, 2001.
PCT International Search Report for PCT/US99/18289, 1 pg, Mailed Dec. 7, 1999.
PCT Notification of International Preliminary Examination Report for PCT/US99/18289, 4 pgs, Mailed Jul. 7, 2000.
European Search Report for EP 99945039.8, 3 pgs, Oct. 1, 2001.
PCT International Search Report for PCT/US02/19261, 1 pg, Mailed Sep. 18, 2002.
PCT International Preliminary Examination Report for PCT/US02/19261, 3 pgs, Mar. 25, 2003.
PCT International Search Report for PCT/US02/29476, 1 pg, Mailed May 24, 2004.
PCT International Search Report for PCT/US03/13686, 1 pg, Mailed Nov. 25, 2003.
PCT International Search Report for PCT/US04/03614, 1 pg, Mailed Sep. 14, 2004.
PCT Written Opinion of the International Searching Authority for PCT/US04/03614, 4 pgs, Mailed Sep. 14, 2004.
EP Communication, European Examination Report for EP 98953859.0, 3 pgs, Jun. 14, 2004.
EP Communication, European Examination Report for EP 99945039.8, 5 pgs, May 10, 2004.
PCT Notification of International Search Report and Written Opinion for PCT/US06/26321, 8pgs, Mailed Apr. 25, 2007.
PCT Notification of the International Search Report and Written Opinion for PCT/US06/60618, 7pgs, Mailed Oct. 5, 2007.
Barry et al., "The Effect of Radiofrequency-generated Thermal Energy on the Mechanical and Histologic Characteristics of the Arterial Wall in Vivo: Implications of Radiofrequency Angioplasty" American Heart Journal vol. 117, pp. 332-341, 1982.
Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC-III Instruction Manual", 15 pgs, Jul. 1991.
Cook et al., "Therapeutic Medical Devices: Application and Design", Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" Bio-Medical Engineering vol. 4, pp. 206-216, May 1969.
Elsasser, V.E. et al., "An Instrument for Transurethral Resection without Leakage of Current" Acta Medicotechnica vol. 24, No. 4, pp. 129-134, 1976.
Geddes, "Medical Device Accidents: With Illustrative Cases" CRC Press, 3 pgs, 1998.
Honig, W., "The Mechanism of Cutting in Electrosurgery" IEEE pp. 58-65, 1975.
Kramolowsky et al. "The Urological App of Electorsurgery" J. of Urology vol. 146, pp. 669-674, 1991.
Kramolowsky et al. "Use of 5F Bipolar Electrosurgical Probe in Endoscopic Urological Procedures" J. of Urology vol. 143, pp. 275-277, 1990.
Lee, B et al. "Thermal Compression and Molding of Artherosclerotic Vascular Tissue with Use" JACC vol. 13(5), pp. 1167-1171, 1989.
Letter from Department of Health to Jerry Malis dated Jan. 24, 1991, 3 pgs.
Letter from Department of Health to Jerry Malis dated Jul. 25, 1985, 1 pg.

Letter from Jerry Malis to FDA dated Jul. 25, 1985, 2 pgs.
Lu, et al., "Electrical Thermal Angioplasty: Catheter Design Features, In Vitro Tissue Ablation Studies and In Vitro Experimental Findings," *Am J. Cardiol* vol. 60, pp. 1117-1122, Nov. 1, 1987.
Malis, L., "Electrosurgery, Technical Note," *J. Neursurg.*, vol. 85, pp. 970-975, Nov. 1996.
Malis, L., "Excerpted from a seminar by Leonard I. Malis, M.D. at the 1995 American Association of Neurological Surgeons Meeting," 1pg, 1995.
Malis, L., "Instrumentation for Microvascular Neurosurgery" *Cerebrovascular Surgery*, vol. 1, pp. 245-260, 1985.
Malis, L., "New Trends in Microsurgery and Applied Technology," *Advanced Technology in Neurosurgery*, pp. 1-16, 1988.
Malls, L., "The Value of Irrigation During Bipolar Coagulation" See ARTC 21602, 1 pg, Apr. 9, 1993.
Nardella, P.C., *SPIE* 1068: pp. 42-49, Radio Frequency Energy and Impedance Feedback, 1989.
O'Malley, Schaum's Outline of Theory and Problems of Basic Circuit Analysis, McGraw-Hill, $2^{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John A., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" *Gastroenterology* vol. 74(3), pp. 527-534, 1978.
Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.
Ramsey et al., "A Comparison of Bipolar and Monopolar Diathermy Probes in Experimental Animals", *Urological Research* vol. 13, pp. 99-102, 1985.
Selikowitz et al., "Electric Current and Voltage Recordings on the Myocardium During Electrosurgical Procedures in Canines," *Surgery, Gynecology & Obstetrics*, vol. 164, pp. 219-224, Mar. 1987.
Shuman, "Bipolar Versus Monopolar Electrosurgery: Clinical Applications," *Dentistry Today*, vol. 20, No. 12, 7 pgs, Dec. 2001.
Slager et al. "Spark Erosion of Arteriosclerotic Plaques" *Z. Kardiol.* 76:Suppl. 6, pp. 67-71, 1987.
Slager et al. "Vaporization of Atherosclerotice Plaques by Spark Erosion" *JACC* 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.
Stoffels, E. et al., "Biomedical Applications of Plasmas", Tutorial presented prior to the $55^{th}$ Gaseous Electronics Conference in Minneapolis, MN, 41 pgs, Oct. 14, 2002.
Stoffels, E. et al., "Plasma Interactions with Living Cells", Eindhoven University of Technology, 1 pg, 2002.
Stoffels, E. et al., "Superficial Treatment of Mammalian Cells using Plasma Needle", J. Phys. D: Appl. Phys. 26, pp. 2908-2913, Nov. 19, 2003.
Stoffels, E. et al., "Plasma Needle", Eindhoven University of Technology, 1 pg, Nov. 28, 2003.
Stoffels, E. et al., "Plasma Physicists Move into Medicine", Physicsweb, 1 pg, Nov. 2003.
Stoffels, E. et al., "Plasma Treated Tissue Engineered Skin to Study Skin Damage", Biomechanics and Tissue Engineering, Materials Technology, 1 pg, 2003.
Stoffels, E. et al., "Plasma Treatment of Dental Cavities: A Feasibility Study", IEEE Transaction on Plasma Science, vol. 32, No. 4, pp. 1540-1542, Aug. 2004.
Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.

Stoffels, E. et al., "Electrical and Optical Characterization of the Plasma Needle", New Journal of Physics 6, pp. 1-14, Oct. 28, 2004.
Stoffels, E. et al., "Where Plasma Meets Plasma", Eindhoven University of Technology, 23 pgs, 2004.
Stoffels, E. et al., "Gas Plasma effects on Living Cells", Physica Scripta, T107, pp. 79-82, 2004.
Stoffels, E. et al., "Plasma Treatment of Mammalian Vascular Cells: A Quantitative Description", IEEE Transaction on Plasma Science, vol. 33, No. 2, pp. 771-775, Apr. 2005.
Stoffels, E. et al., "Deactivation of *Escherichia coli* by the Plasma Needle", J. Phys. D: Appl. Phys. 38, pp. 1716-1721, May 20, 2005.
Stoffels, E. et al., "Development of a Gas Plasma Catheter for Gas Plasma Surgery", XXVIIth ICPIG, Endoven University of Technology, pp. 18-22, Jul. 2005.
Stoffels, E. et al., "Development of a Smart Positioning Sensor for the Plasma Needle", Plasma Sources Sci. Technol. 15, pp. 582-589, Jun. 27, 2006.
Stoffels, E. et al., Killing of S. Mutans Bacteria Using a Plasma Needle at Atmospheric Pressure, IEEE Transaction on Plasma Science, vol. 34, No. 4, pp. 1317-1324, Aug. 2006.
Stoffels, E. et al., "Plasma-Needle Treatment of Substrates with Respect to Wettability and Growth of *Excherichia coli* and *Streptococcus Mutans*", IEEE Transaction on Plasma Science, vol. 34, No. 4, pp. 1325-1330, Aug. 2006.
Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.
Stoffels, E. et al.; "UV Excimer Lamp Irradiation of Fibroblasts: The Influence on Antioxidant Homostasis", IEEE Transaction on Plasma Science, vol. 34, No. 4, pp. 1359-1364, Aug. 2006.
Stoffels, E. et al., "Plasma Needle for In Vivo Medical Treatment: Recent Developments and Perspectives", Plasma Sources Sci. Technol. 15, pp. S169-S180, Oct. 6, 2006.
Swain, C.P., et al., "Which Electrode, A Comparison of four endoscopic methods of electrocoagulation in experimental bleeding ulcers" *Gut* vol. 25, pp. 1424-1431, 1987.
Tucker, R. et al. "A Comparison of Urologic Application of Bipolar Versus Monopolar Five French Electrosurgical Probes" *J. of Urology* vol. 141, pp. 662-665, 1989.
Tucker, R. et al. "In vivo effect of 5 French Bipolar and Monopolar Electrosurgical Probes on the Porcine Bladder" *Urological Research* vol. 18, pp. 291-294, 1990.
Tucker, R. et al., "Demodulated Low Frequency Currents from Electrosurgical Procedures," *Surgery, Gynecology and Obstetrics*, 159:39-43, 1984.
Tucker, R. et al., Abstract P14-11, p. 248, "A Bipolar Electrosurgical Turp Loop", Nov. 1989.
Valley Forge Scientific Corp., "Summary of Safety and Effective Information from 510K", 2pgs, 1991.
Valley Forge's New Products, CLINICA, 475, 5, Nov. 6, 1991.
Valleylab SSE2L Instruction Manual, 11 pgs, Jan. 6, 1983.
Valleylab, Inc. "Valleylab Part No. 945 100 102 A" Surgistat Service Manual, pp. 1-46, Jul. 1988.
Wattiez, Arnaud et al., "Electrosurgery in Operative Endoscopy," Electrosurgical Effects, Blackwell Science, pp. 85-93, 1995.
Wyeth, "Electrosurgical Unit" pp. 1181-1202, 1990.
European Examination Report for EP 02773432 4 pgs, Sep. 22, 2009.
European Examination Report for EP 04708664 7pgs, Sep. 7, 2009.
European Examination Report for EP 02749601.7 4pgs, Dec. 2, 2009.
European Examination Report 2 for EP 04708664 5pgs, May 3, 2010.
Extended European Search Report for EP09152846, 8pgs, Jan. 5, 2010.
European Search Report for EP 09152850, 2 pgs, Dec. 29, 2009.
UK Search Report for GB0900604.0, 4 pgs, May 15, 2009.

* cited by examiner

ABLATION APPARATUS HAVING REDUCED NERVE STIMULATION AND RELATED METHODS

FIELD OF THE INVENTION

The present invention relates to electrosurgical instruments which are configured to reduce or eliminate nerve stimulation in tissue. More particularly, the present invention relates to electrosurgical instruments having multiple electrodes which are configured to reduce or eliminate nerve stimulation in neuromuscular structures.

BACKGROUND OF THE INVENTION

Electrosurgery typically utilizes the application of high frequency currents to cut or ablate tissue structures, either utilizing a monopolar or bipolar configuration. Monopolar configurations utilize an instrument having a single electrode and rely on externally connected return electrode placed on the patient whereas bipolar configurations utilize both an active and return electrode on the instrument itself for application of a current between the electrodes.

Electrosurgical procedures and techniques are particularly useful in reducing patient bleeding and trauma typically associated with surgical procedures. However, the radio frequency (RF) currents typically used by electrosurgical instruments during procedures can sometimes induce involuntary and undesired stimulation in nearby neuromuscular structures causing discomfort to the patient as well as compromising the safety of the patient. Attempts to avoid such undesired stimulation have included increasing the operating frequency of the electrosurgical generator to mitigate the stimulating effects of the current. Other attempts have included reducing the rate of change of the output voltage or reducing the overall magnitude of the RF voltage and current.

Increasing the operating frequency may increase the costs associated with the power supply as well as compromise the performance of the electrosurgical instrument. Moreover, an increase in operating frequency may also increase the magnitude of undesired RF leakage currents. Likewise, limiting the rate of change of the output voltage or reducing the magnitude could also degrade instrument performance because such a limitation or reduction may limit the response time of the electrosurgical system or limit the total power delivered to the target tissue.

Mitigating or eliminating undesired electrical stimulation in surrounding structures may be particularly useful in procedures where electrosurgical instruments are used in electrically conductive environments, particularly regions which may be filled with blood, irrigated with saline, or the like. In these types of operating environments, such instruments may be utilized to cut and/or ablate tissue, such as articular cartilage, meniscal tissue, etc.

Accordingly, there is a need for electrosurgical instruments which can deliver sufficient power to targeted tissue while reducing the magnitude of RF current delivered not only to the tissue but also to surrounding structures so as to mitigate or eliminate undesired stimulation.

SUMMARY OF THE INVENTION

An electrosurgical instrument used to treat tissue within a patient body space may be configured to electrically isolate pairs of active and return electrodes from other pairs of electrodes on the instrument to create at least two opposing currents which effectively cancel one another. This may be accomplished such that any net current flow is inhibited from developing within surrounding tissue structures thereby mitigating or eliminating undesired electrical stimulation of the tissue.

An example of an electrode configuration includes a first and second pair of electrodes positioned along an instrument shaft separated physically and isolated electrically from one another such that any current passing through one or both active electrodes is separate from one another and directed to flow to its respective return electrode, i.e., a first current flows between the first active electrode and first return electrode and a second current flows between the second active electrode and the second return electrode.

Another example may include the first active electrode positioned adjacent to the second active electrode along the shaft such that the first return electrode is positioned proximal to both active electrodes and the second return electrode is positioned distal to both active electrodes. In this variation, the second active electrode may be positioned between the first active electrode and the first return electrode, while the first active electrode may be positioned between the second active electrode and the second return electrode. Other electrode pair configurations may be utilized and are intended to be within this disclosure.

In these or any other electrode configurations, the electrode pairs may be powered by respective output circuits. Two respective output circuits may each comprise a separate secondary coil on a transformer where a single primary circuit having a current may induce currents in each respective electrode pair. The secondary coils of the first electrode pair may be arranged to induce a first current in a first direction flowing from the first return electrode to the first active electrode. Similarly, the secondary coils of the second electrode pair may be arranged to induce a second current in a second direction opposite to the first direction flowing from the second active electrode to the second return electrode. Because of the arrangement of the secondary coils for each respective electrode pair, the resulting opposing output signals may be equal but are 180° out-of-phase with respect to one another.

Because these output circuits are electrically isolated from one another, the possibility for current to flow from one circuit to the other may be reduced or eliminated entirely. With these opposing output currents, there may be a cancellation effect of the current at a distance in the surrounding tissue sufficiently removed from the electrodes such that there is a reduction in the tendency to create undesired electrical stimulation in nearby tissue structures. At a distance of several electrode diameters away from the instrument, any tissue surface parallel to the device profile should not have a tendency to develop any net current flow.

DETAILED DESCRIPTION OF THE INVENTION

Figure 1:
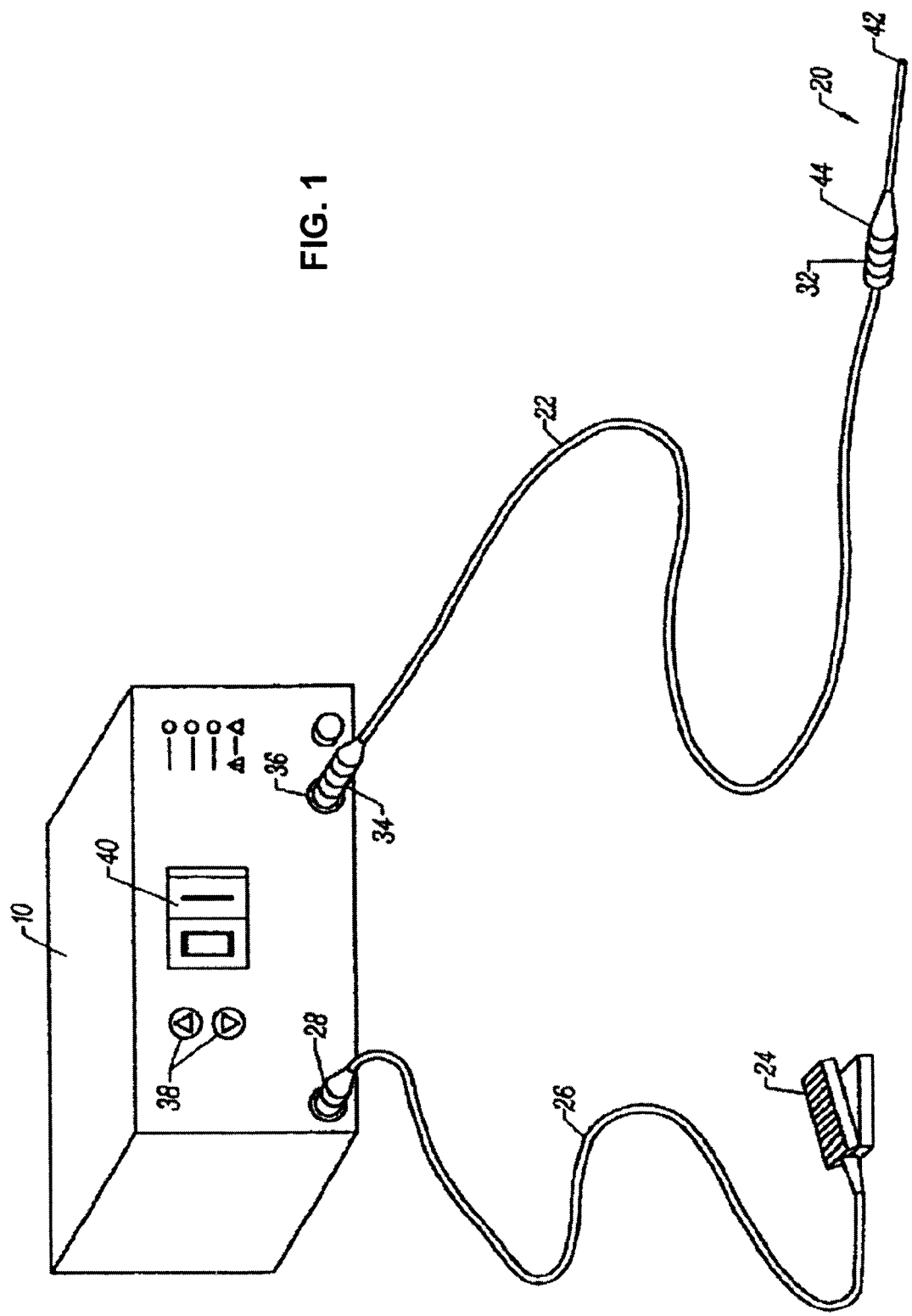
FIG. 1 shows an exemplary electrosurgical system for an instrument configured to treat various tissue regions.

High frequency (RF) electrical energy may be applied to one or more pairs of electrodes, e.g., in the presence of electrically conductive fluid such as saline to remove and/or modify the structure of tissue structures. Generally, an electrosurgical instrument may be configured to electrically isolate each pair of active and return electrodes from other pairs of electrodes. Thus, electrode configuration on the surgical device may be designed to create at least two opposing currents which effectively cancel one another such that any net current flow is inhibited from developing within surrounding tissue structures thereby mitigating or eliminating undesired electrical stimulation.

In many electrosurgical procedures, a high frequency voltage difference is applied between the active electrode(s) and one or more return electrode(s) to develop high electric field intensities in the vicinity of the target tissue site. The high electric field intensities lead to electric field induced molecular breakdown of target tissue through molecular dissociation (rather than thermal evaporation or carbonization). This molecular disintegration completely removes the tissue structure, as opposed to dehydrating the tissue material by the removal of liquid from within the cells of the tissue, as is typically the case with electrosurgical desiccation and vaporization.

The high electric field intensities may be generated by applying a high frequency voltage that is sufficient to vaporize an electrically conductive fluid over at least a portion of the active electrode(s) in the region between the distal tip of the active electrode(s) and the target tissue. The electrically conductive fluid may be a gas or liquid, such as isotonic saline, delivered to the target site, or a viscous fluid, such as a gel, that is located at the target site. In the latter embodiment, the active electrode(s) are submersed in the electrically conductive gel during the surgical procedure. Since the vapor layer or vaporized region has relatively high electrical impedance, it minimizes the current flow into the electrically conductive fluid. This ionization, under optimal conditions, induces the discharge of energetic electrons and photons from the vapor layer to the surface of the target tissue. A more detailed description of this phenomenon, termed Coblation®, can be found in commonly assigned U.S. Pat. No. 5,683,366 the complete disclosure of which is incorporated herein by reference in its entirety.

The systems and methods for selectively applying electrical energy to a target location within or on a patient's body may be accomplished particularly in procedures where the tissue site is flooded or submerged with an electrically conductive fluid, such as during arthroscopic surgery of the knee, shoulder, ankle, hip, elbow, hand, foot, etc. Other tissue regions which may be treated by the system and methods described herein may also include, but are not limited to, prostate tissue, and leiomyomas (fibroids) located within the uterus, gingival tissues and mucosal tissues located in the mouth, tumors, scar tissue, myocardial tissue, collagenous tissue within the eye or epidermal and dermal tissues on the surface of the skin, etc. Other procedures which may be performed may also include laminectomy/diskectomy procedures for treating herniated disks, decompressive laminectomy for stenosis in the lumbosacral and cervical spine, removal of a portion of the nucleus pulposus, removal of intervertebral tissue, posterior lumbosacral and cervical spine fusions, treatment of scoliosis associated with vertebral disease, foraminotomies to remove the roof of the intervertebral foramina to relieve nerve root compression, as well as anterior cervical and lumbar diskectomies. Tissue resection within accessible sites of the body that are suitable for electrode loop resection, such as the resection of prostate tissue, leiomyomas (fibroids) located within the uterus, and other diseased tissue within the body, may also be performed Other procedures which may be performed where multiple tissue types are present may also include, e.g., the resection and/or ablation of the meniscus and the synovial tissue within a joint during an arthroscopic procedure. It will be appreciated that the systems and methods described herein can be applied equally well to procedures involving other tissues of the body, as well as to other procedures including open procedures, intravascular procedures, urology, laparoscopy, arthroscopy, thoracoscopy or other cardiac procedures, dermatology, orthopedics, gynecology, otorhinolaryngology, spinal and neurologic procedures, oncology, and the like.

The electrosurgical instrument may comprise a shaft or a handpiece having a proximal end and a distal end which supports the one or more active electrodes. The shaft or handpiece may assume a wide variety of configurations, with the primary purpose being to mechanically support the active electrode and permit the treating physician to manipulate the electrodes from a proximal end of the shaft. The shaft may be rigid or flexible, with flexible shafts optionally being combined with a generally rigid external tube for mechanical support. The distal portion of the shaft may comprise a flexible material, such as plastics, malleable stainless steel, etc, so that the physician can mold the distal portion into different configurations for different applications. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft. Thus, the shaft may typically have a length between at least 5 cm and at least 10 cm, more typically being 20 cm or longer for endoscopic procedures. The shaft may typically have a diameter of at least 0.5 mm and frequently in the range of from about 1 mm to 10 mm. Also, in various procedures, the shaft may have any suitable length and diameter that would facilitate handling by the surgeon.

As mentioned above, a gas or fluid is typically applied to the target tissue region and in some procedures it may also be desirable to retrieve or aspirate the electrically conductive fluid after it has been directed to the target site. In addition, it may be desirable to aspirate small pieces of tissue that are not completely disintegrated by the high frequency energy, air bubbles, or other fluids at the target site, such as blood, mucus, the gaseous products of ablation, etc. Accordingly, the instruments described herein can include a suction lumen in the probe or on another instrument for aspirating fluids from the target site.

Referring to FIG. 1, an exemplary electrosurgical system for a single instrument having multiple electrodes configured to treat varying tissue regions is illustrated in the assembly. As shown, the electrosurgical system may generally comprise an electrosurgical probe 20 connected to a power supply 10 for providing high frequency voltage to the active electrodes. Probe 20 includes a connector housing 44 at its proximal end, which can be removably connected to a probe receptacle 32 of a probe cable 22. The proximal portion of cable 22 has a connector 34 to couple probe 20 to power supply 10 to power the multiple electrodes of electrode assembly 42 positioned near or at the distal end of probe 20. In another variation, the cable and handle are integrated together as one part.

Power supply 10 has an operator controllable voltage level adjustment 38 to change the applied voltage level, which is observable at a voltage level display 40. Power supply 10 may also include one or more foot pedals 24 and a cable 26 which is removably coupled to a receptacle with a cable connector 28. The foot pedal 24 may also include a second pedal (not shown) for remotely adjusting the energy level applied to the active electrodes and a third pedal (also not shown) for switching between an ablation mode and a coagulation mode or for switching to activate between electrodes. Operation of and configurations for the power supply 10 are described in further detail in U.S. Pat. No. 6,746,447, which is incorporated herein by reference in its entirety.

The voltage applied between the return electrodes and the active electrodes may be at high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the active electrode size, the operating frequency and the operation mode of the particular procedure or desired effect on the tissue (i.e., contraction, coagulation or ablation). Typically, the peak-to-peak voltage will be in the range of 10 to 2000 volts, preferably in the range of 20 to 1200 volts and more preferably in the range of about 40 to 800 volts (again, depending on the electrode size, the operating frequency and the operation mode).

The power source may be current limited or otherwise controlled so that undesired heating of the target tissue or surrounding (non-target) tissue does not occur. In one variation, current limiting inductors are placed in series with each independent active electrode, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in PCT application WO 94/026228, which is incorporated herein by reference in its entirety.

Additionally, current limiting resistors may be selected. These resistors will have a large positive temperature coefficient of resistance so that, as the current level begins to rise for any individual active electrode in contact with a low resistance medium (e.g., saline irrigant or conductive gel), the resistance of the current limiting resistor increases significantly, thereby minimizing the power delivery from the active electrode into the low resistance medium (e.g., saline irrigant or conductive gel).

Figure 2:
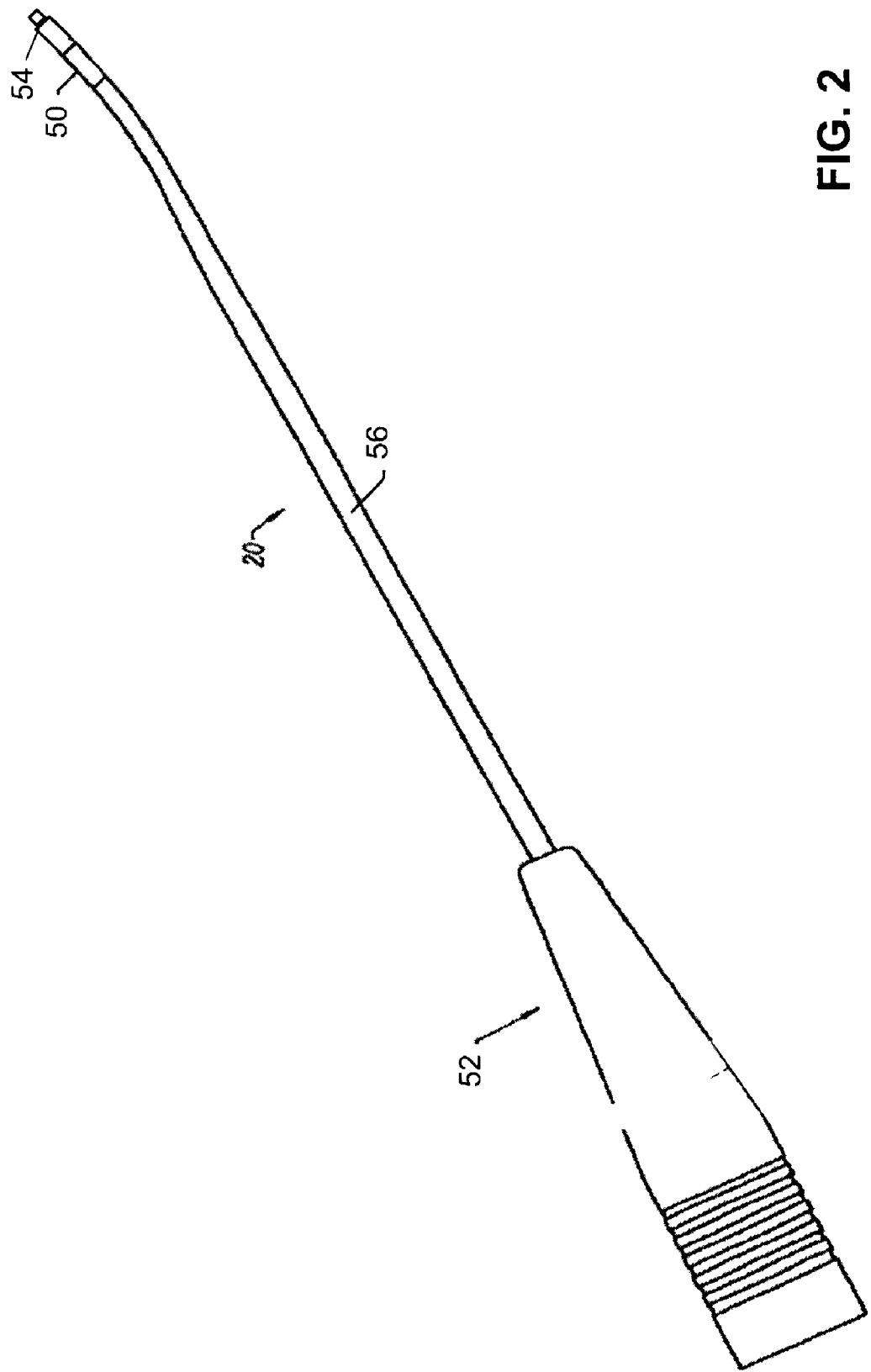
FIG. 2 illustrates an exemplary electrosurgical probe which generally includes an elongated shaft which may be flexible or rigid, a handle coupled to the proximal end of shaft and a multi-electrode assembly.

FIG. 2 illustrates an exemplary electrosurgical probe 20 which generally includes an elongated shaft 50 which may be flexible or rigid, a handle 52 coupled to the proximal end of shaft 50 and a multi-electrode assembly 54, described in further detail below, coupled to the distal end of shaft 50. Shaft 50 may comprise an electrically conducting material, such as metal, which may be selected from the group consisting of, e.g., tungsten, stainless steel alloys, platinum or its alloys, titanium or its alloys, molybdenum or its alloys, and nickel or its alloys. Shaft 50 also includes an electrically insulating jacket 56, which is typically formed as one or more electrically insulating sheaths or coatings, such as polytetrafluoroethylene, polyimide, and the like. The provision of the electrically insulating jacket over the shaft prevents direct electrical contact between these metal elements and any adjacent body structure or the surgeon. Such direct electrical contact between a body structure (e.g., tendon) and an exposed electrode could result in unwanted heating of the structure at the point of contact causing necrosis.

Handle 52 typically comprises a plastic material that is easily molded into a suitable shape for handling by the surgeon. Moreover, the distal portion of shaft 50 may be bent to improve access to the operative site of the tissue being treated (e.g., contracted). In alternative embodiments, the distal portion of shaft 50 comprises a flexible material which can be deflected relative to the longitudinal axis of the shaft. Such deflection may be selectively induced by mechanical tension of a pull wire, for example, or by a shape memory wire that expands or contracts by externally applied temperature changes. A more complete description of this embodiment can be found in PCT application WO 94/026228, which has been incorporated by reference above.

The bend in the distal portion of shaft 50 is particularly advantageous in arthroscopic treatment of joint tissue as it allows the surgeon to reach the target tissue within the joint as the shaft 50 extends through a cannula or portal. Of course, it will be recognized that the shaft may have different angles depending on the procedure. For example, a shaft having a 90° bend angle may be particularly useful for accessing tissue located in the back portion of a joint compartment and a shaft having a 10° to 30° bend angle may be useful for accessing tissue near or in the front portion of the joint compartment.

Regardless of the bend angle, an electrode assembly having multiple, e.g., two or more, actuatable electrodes disposed near or at the distal end of shaft 50 may be utilized. General difficulties in designing electrosurgical devices with relatively large active electrodes typically entail delivering a relatively high level of RF energy until ablative effects are activated at the electrodes. However, once the ablative effects are activated, the load impedance increases and the power delivery to the tissue decreases. Thus, a multi-electrode assembly may be configured to effectively deliver the energy to a tissue region of interest.

Figure 3:
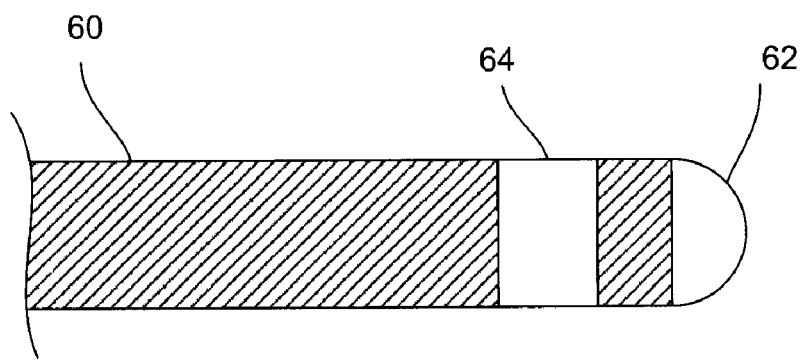
FIG. 3 shows a detail side view of a typical electrosurgical RF instrument having a single active electrode and return electrode.

Turning now to FIG. 3, a detail side view of a conventional RF instrument which may be disposed at the distal end of the instrument shaft is shown. Shaft 60 is illustrated as having a bipolar electrode configuration with active electrode 62 disposed upon the distal tip of the shaft 60 and return electrode 64 disposed proximal to and electrically insulated from active electrode 62. The current that is applied flows between active and return electrodes 62, 64 to affect tissue treatment. Such a configuration may allow for some of the current to be inadvertently discharged into the surrounding tissues thereby inducing electrical stimulation of the tissue, particularly neuromuscular tissue structures.

Figure 4:
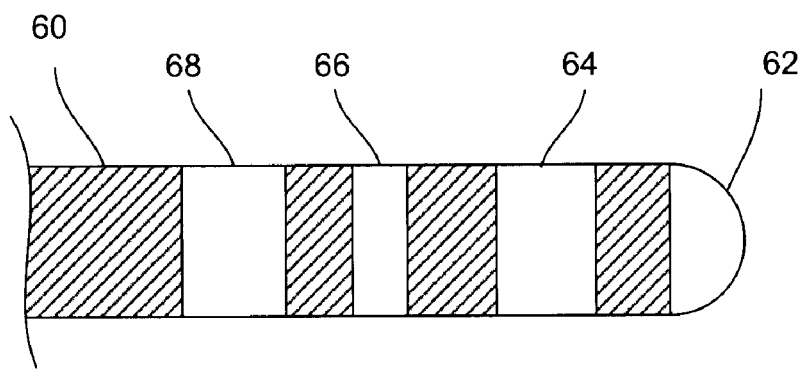
FIG. 4 shows a detail side view an electrosurgical instrument having at least one additional pair of electrodes which are electrically isolated from the first pair and which are configured to operate out-of-phase with respect to the first pair of electrodes.

FIG. 4 illustrates an example of another electrode configuration where a second pair of electrodes may be positioned along shaft 60 proximal to the first pair of electrodes. As shown, second active electrode 66 and second return electrode 68 may be separated physically and isolated electrically from the first pair of electrodes 62, 64 such that any current passing through one or both active electrodes 62, 66 is separate from one another and directed to flow to its respective return electrode, i.e., a first current flows between first active electrode 62 and first return electrode 64 and a second current flows between second active electrode 66 and second return electrode 68. Second active electrode 66 may be positioned proximal to first return electrode 64 and second return electrode 68 may be positioned proximal to second active electrode 66.

Figure 5:
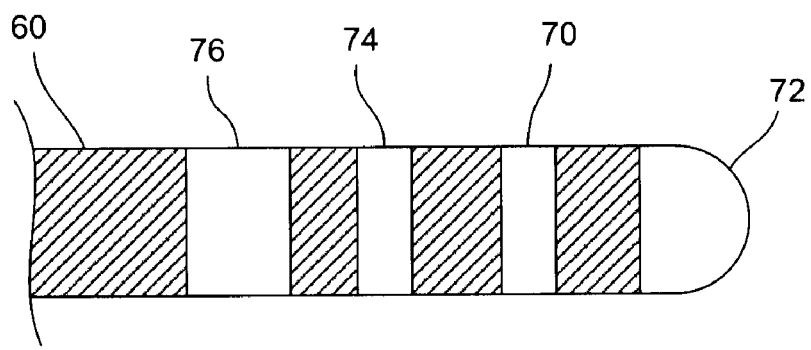
FIG. 5 shows a detail side view of another variation where the active and return electrodes may be alternated on one of the pairs of electrodes.

FIG. 5 shows another example where first active electrode 70 may be positioned adjacent to second active electrode 74 along shaft 60 such that first return electrode 76 is positioned proximal to both active electrodes 70, 74 and second return electrode 72 is positioned distal to both active electrodes 70, 74. In this variation, second active electrode 74 may be positioned between first active electrode 70 and first return electrode 76, while first active electrode 70 may be positioned between second active electrode 74 and second return electrode 72 along shaft 60. This particular electrode configuration is shown as an illustrative example and other electrode pair configurations may be utilized and are intended to be within this disclosure.

Figure 6:
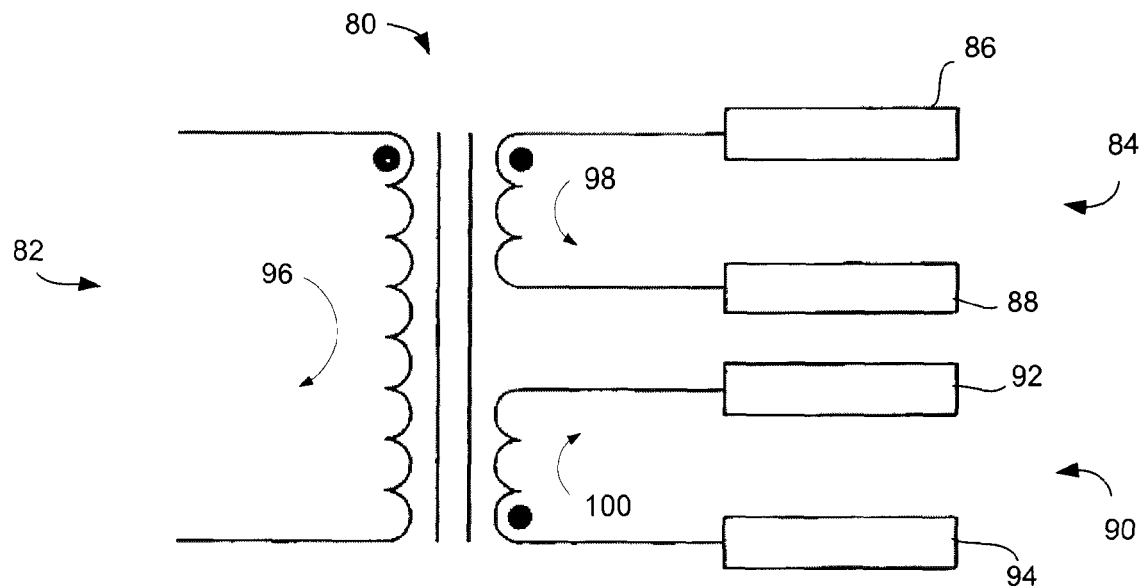
FIG. 6 illustrates a schematic representation of a single primary current which may be used to induce opposing secondary currents in at least two electrode assemblies which are electrically isolated from one another to create the output from the electrodes pairs which are out-of-phase with respect to one another.

In these or any other electrode configurations, the electrode pairs may be powered by respective output circuits. In the example utilizing at least two electrode pairs, two respective output circuits may each comprise a separate secondary coil on a transformer. As illustrated in the schematic representation 80 of FIG. 6, a single primary circuit 82 having a current 96 may induce currents in each respective electrode pair, e.g., first electrode pair 84 and second electrode pair 90. The secondary coils of first electrode pair 84 may be arranged to induce a first current 98 in a first direction flowing from first return electrode 88 to first active electrode 86. Similarly, the secondary coils of second electrode pair 90 may be arranged to induce a second current 100 in a second direction opposite to the first direction flowing from second active electrode 92 to second return electrode 94. Because of the arrangement of the secondary coils for each respective electrode pair 84, 90, the resulting opposing output signals may be equal but are 180° out-of-phase with respect to one another.

Figure 7:
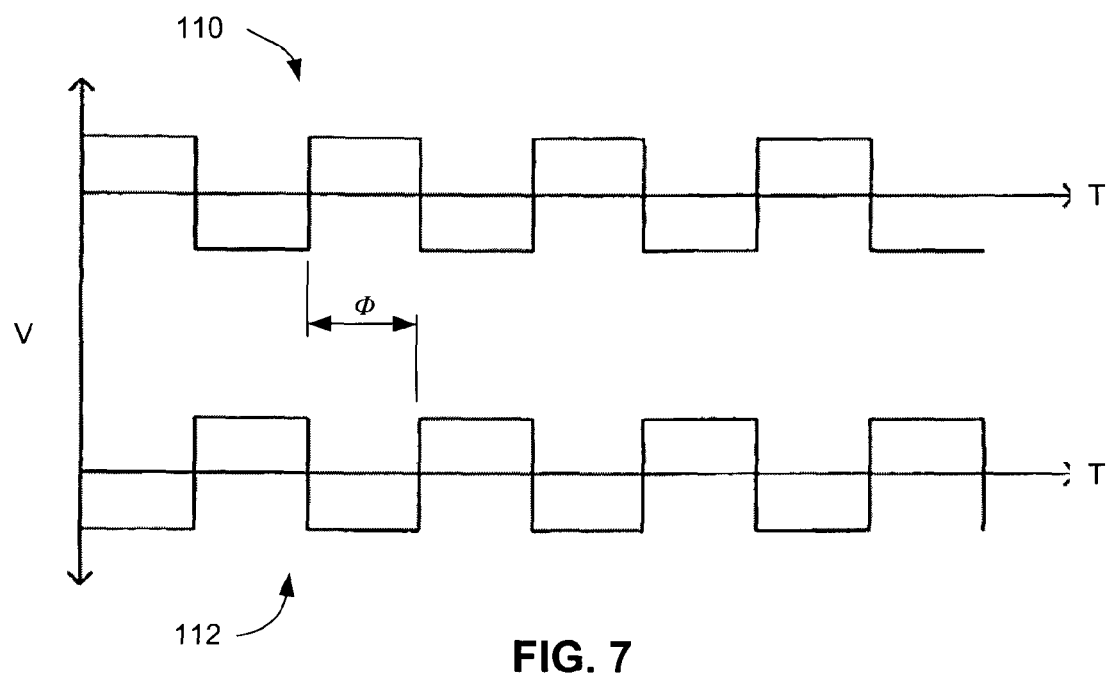
FIG. 7 graphically illustrates the output waveforms which are out-of-phase with respect to one another.

This is graphically illustrated in FIG. 7 which shows one example of the output waveform 110 from first electrode pair 84 in relation to the output waveform 112 from second electrode pair 90. The amplitude of each output voltage waveform 110, 112 may be equivalent but they are shifted at a phase angle, Φ, in this example 180° out-of-phase with respect to one another. Because these output circuits are electrically isolated from one another, the possibility for current to flow from one circuit to the other may be reduced or eliminated entirely. With these opposing output currents, there may be a cancellation effect of the current at a distance in the surrounding tissue sufficiently removed from the electrodes such that there is a reduction in the tendency to create undesired electrical stimulation in nearby tissue structures. At a distance of several electrode diameters away from the instrument, any tissue surface parallel to the device profile should not have a tendency to develop any net current flow.

In other examples, it may be possible to change the configuration of the output circuit to allow individual control of each output circuit to allow a device that targets different anatomical structures where different active electrode sizes or configurations are more optimal. These separate output circuits could also be used to vary the application time at each electrode pair in order to create different effects in the area surrounding each electrode pair. Additionally, these output circuits could be designed to provide different effects at each location, e.g., a distal electrode pair may be configured to perform a cutting operation to gain access to the targeted anatomy while a more proximal pair may be configured to provide a coagulation effect.

Figure 8:
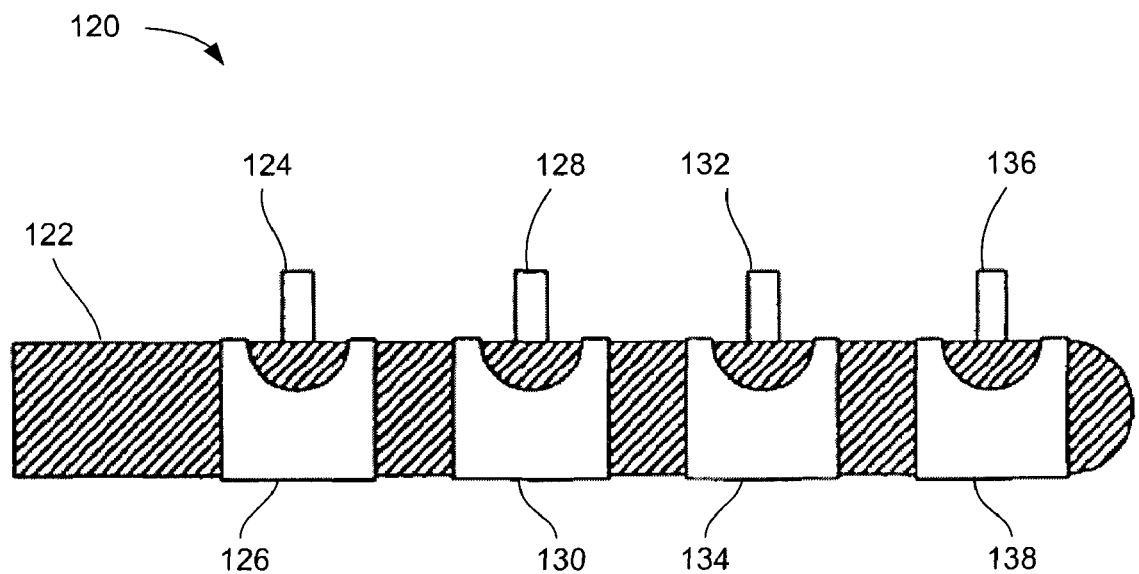
FIG. 8 shows another example of an electrode configuration utilizing multiple electrodes.

Additional exemplary electrode configurations utilizing separate and isolated electrode outputs are shown in FIG. 8 in the side view of electrode assembly 120. In this example, shaft 122 may have at least four electrode pairs disposed therealong where each active electrode may be positioned along shaft 122 with each return electrode positioned around each respective active electrode. For example, first active electrodes 124, 132 may have respective return electrodes 126, 134 in an alternating configuration with second active electrodes 128, 136 having respective return electrodes 130, 138.

Figure 9:
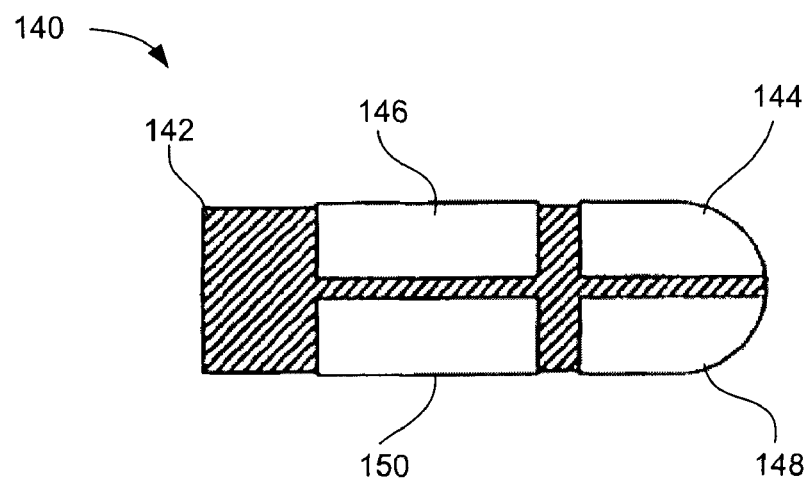
FIG. 9 shows another example of an electrode configuration utilizing multiple electrodes.

FIG. 9 illustrates yet another configuration 140 where shaft 142 may have first active electrode 144 disposed along a portion of the distal tip of shaft 142 adjacent to and electrically insulated from second active electrode 148 also disposed along the distal tip of shaft 142. First return electrode 146 may be located proximal to first active electrode 144 also adjacent to and electrically insulated from second return electrode 150. As above, each electrode pair is electrically isolated from one another and may have the output current flowing in opposing directions with respect to one another. The electrodes may take a wide variety of shapes, such as, but not limited to, thin and elongate, solid or hollow, tubular, annular, cylindrical, curved, ribboned, plate or bowl-shaped, etc. The electrodes, when not a portion of the shaft itself, may be attached to the shaft with a weld, press-fit, adhesive, tack, and/or wire such as a ball wire. Redundant joints (namely, a joint having more than one feature or mechanism to affix the components) may be used to hold the electrodes onto the shaft.

Other modifications and variations can be made to the disclosed embodiments without departing from the subject invention. For example, other numbers and arrangements of the active electrodes and their methods for use are possible. Similarly, numerous other methods of ablating or otherwise treating tissue using electrosurgical probes will be apparent to the skilled artisan. Moreover, the instruments and methods described herein may be utilized in other regions of the body (e.g., shoulder, knee, etc.) and for other tissue treatment procedures (e.g., chondroplasty, meniscectomy, etc.). Thus, while the exemplary embodiments have been described in detail, by way of example and for clarity of understanding, a variety of changes, adaptations, and modifications will be obvious to those of skill in the art. Therefore, the scope of the present invention is limited solely by the appended claims.

What is claimed is:

1. An electrosurgical instrument electrically coupled to a primary input circuit of a power supply transformer and configured to inhibit electrical stimulation of surrounding tissue structures, comprising:

a first electrode pair electrically connected to a first output coil of the transformer, the primary input circuit inducing a first current in the first output coil and thereby a first voltage waveform between the first electrode pair; and a second electrode pair electrically isolated from the first electrode pair and disposed adjacent to the first electrode pair, wherein the second electrode pair is electrically connected to a second output coil of the transformer, wherein the second output coil is electrically isolated from the first output coil and the primary input circuit induces a second current in the second electrode pair and thereby a second voltage waveform between the second electrode pair which is out of phase with the first voltage waveform.

2. The instrument of claim 1 further comprising an elongated shaft upon which the first and second electrode pairs are positioned adjacent to one another.

3. The instrument of claim 1 wherein the first electrode pair comprises at least one active electrode and at least one return electrode.

4. The instrument of claim 1 wherein the second electrode pair comprises at least one active electrode and at least one return electrode.

5. The instrument of claim 1 wherein an amplitude of the first voltage waveform is equal to an amplitude of the second voltage waveform.

6. The instrument of claim 1 wherein the first electrode pair has a current flowing from a first active electrode to a first return electrode.

7. The instrument of claim 1 wherein an amplitude of the first current is equal to an amplitude of the second current.

8. The instrument of claim 1 wherein the first and second voltage waveforms are 180° out-of-phase compared to one another.

9. A method of reducing or eliminating a net current in tissue structures adjacent to an electrosurgical instrument, comprising:

positioning an electrosurgical instrument in proximity to a tissue region to be treated, the electrosurgical instrument having at least a first electrode pair and a second electrode pair adjacent to the first electrode pair, wherein each electrode pair is powered by a separate, electrically isolated output circuit of a power supply transformer;

inducing a first current flowing through the first electrode pair; and inducing a second current flowing through the second electrode pair such that an output of the first current is out-of-phase compared to an output of the second current.

10. The method of claim 9 wherein positioning comprises advancing the electrosurgical instrument within a body space of a patient.

11. The method of claim 10 wherein advancing comprises placing the electrosurgical instrument within a joint space of the patient.

12. The method of claim 9, wherein the tissue region comprises one tissue selected from the group consisting of tonsils, turbinates, disks, vertebral bodies, cartilage, meniscus, fascia, synovial tissue, tendon, and capsular tissue.

13. The method of claim 9, wherein inducing the first current comprises inducing the first current via a power supply common to the first and second electrode pairs.

14. The method of claim 9, wherein inducing the second current comprises inducing the second current to be of equal amplitude compared to the first current.

15. The method of claim 9, wherein the output of the first current is at least 180° out-of-phase compared to the output of the second current.

16. The method of claim 9 further comprising treating the tissue region via the first or second electrode pairs.

17. The instrument of claim 1, wherein the first current travels in the opposite direction to the second current.

* * * * *